United States Patent
Kouji et al.

(10) Patent No.: US 6,496,695 B1
(45) Date of Patent: Dec. 17, 2002

(54) RESOURCE-SAVING EVENT-DRIVEN MONITORING SYSTEM AND METHOD

(75) Inventors: Kurimura Kouji, Tokyo (JP); Okamura Susumu, Ibaraki (JP); Hara Eiichi, Kanagawa (JP); Shoujima Hiroshi, Ibaraki (JP); Unuma Munetoshi, Ibaraki (JP); Ando Masashi, Kanagawa (JP)

(73) Assignee: Hitchi, Ltd., Tokyo (JP)

( * ) Notice: Subject to any disclaimer, the term of this patent is extended or adjusted under 35 U.S.C. 154(b) by 0 days.

(21) Appl. No.: 09/361,597

(22) Filed: Jul. 27, 1999

(30) Foreign Application Priority Data

Jul. 27, 1998 (JP) .......................... 10-210776

(51) Int. Cl.[7] ............................... H04B 7/05
(52) U.S. Cl. .............. 455/427; 455/504; 340/853.2
(58) Field of Search ............... 455/67.1, 67.5, 455/427, 428, 67.7, 68, 456, 3.01, 3.02, 3.03, 3.04, 414, 424; 340/853.2, 853.8, 853.9

(56) References Cited

U.S. PATENT DOCUMENTS

| | | | | |
|---|---|---|---|---|
| 3,972,320 A | * | 8/1976 | Kalman | 128/903 |
| 4,827,943 A | * | 5/1989 | Bornn et al. | 128/903 |
| 4,865,044 A | | 9/1989 | Wallace et al. | 128/736 |
| 5,757,916 A | * | 5/1998 | MacDoran et al. | 342/357.09 |
| 5,969,670 A | * | 10/1999 | Kalafus et al. | 244/183 |
| 6,055,426 A | * | 4/2000 | Beasley | 455/427 |

FOREIGN PATENT DOCUMENTS

| | | |
|---|---|---|
| DE | 2628193 | 12/1977 |
| DE | 4441907 | 6/1995 |
| DE | 19639492 | 5/1997 |
| EP | 760224 | 3/1997 |
| EP | 846440 | 6/1998 |
| JP | 60194601 | 10/1985 |
| JP | 9223930 | 8/1997 |
| JP | 9-251069 | 9/1997 |

OTHER PUBLICATIONS

Unuma, et al., "A recognition of human walking motion by using an accelerometer,", T.IEE Japan, vol. 118–A, No. 3, 1998, pp. 218–226.

* cited by examiner

Primary Examiner—William Trost
Assistant Examiner—Congvan Tran
(74) Attorney, Agent, or Firm—Knoble & Yoshida LLC

(57) ABSTRACT

The event-driven subject monitoring system and method generally include a host unit and a mobile communication unit. These two units communicate via a communication network and are designed to conserve resources at least by operating an event-driven monitoring mobile communication unit.

37 Claims, 14 Drawing Sheets

FIG. 5

| COMMAND NAME | PARAMETERS | | | |
|---|---|---|---|---|
| | 1 | 2 | 3 | 4 |
| COMMAND ARRAY REGISTER START | — | — | — | — |
| COMMAND ARRAY REGISTER END | — | — | — | — |
| COMMAND ARRAY EXEC. START | — | — | — | — |
| CONNECT COMMUNICATION LINE | NUMBER OF REDIAL | REDIAL INTERVAL | — | — |
| DISCONNECT COMMUNICATION LINE | — | — | — | — |
| RESET | TIME(sec) | — | — | — |
| COMMAND ARRAY EXEC. FINISH | — | — | — | — |
| GPS POWER ON | — | — | — | — |
| PPS POWER OFF | — | — | — | — |
| GPS DATA READ | START KEYWORD | NUMBER OF CHARACTERS | NUMBER OF LINES | — |
| POSITION RESULT | TIME OUT PERIOD | NO RESPONSE PERIOD | — | — |
| CONNECT AFTER POSITION RESULT | TIME OUT PERIOD | NO RESPONSE PERIOD | NUMBER OF REDIAL | REDIAL INTERVAL |
| ACCELERATION SENSOR READ | NUMBER OF SAMPLES | SAMPLES INTERVAL | — | — |
| OUTPUT | TEXT OUTPUT | — | — | — |
| EVENT RECOGNITION OUTPUT | — | — | — | — |
| SPECIAL EVENT RECOGNITION | EVENT/ACTION | TIME OUT PERIOD | — | — |
| CONNECT AFTER SPECIAL EVENT RECOGNITION | EVENT/ACTION | TIME OUT PERIOD | NUMBER OF REDIAL | REDIAL INTERVAL |

FIG. 9A

| USER INFORMATION TABLE 31-1 | USER INFORMATION TABLE 31-2 |
|---|---|
| COMMAND ARRAY TRANSMIT FLAG | COMMAND ARRAY TRANSMIT FLAG |
| COMMAND ARRAY TRANSMIT ERROR FLAG | COMMAND ARRAY TRANSMIT ERROR FLAG |
| TERMINAL I.D. | TERMINAL I.D. |
| PHONE NUMBER | PHONE NUMBER |
| NAME | NAME |
| SPOT DATA POINTER | SPOT DATA POINTER |
| NUMBER OF SATELLITES | NUMBER OF SATELLITES |
| SATELLITE INFORMATION POINTER | SATELLITE INFORMATION POINTER |
| ACTION INFORMATION | ACTION INFORMATION |
| ACCELERATION SENSOR THERSHOLD VALUE | ACCELERATION SENSOR THERSHOLD VALUE |
| A PREDETERMINED EVENT/ACTION FILE | A PREDETERMINED EVENT/ACTION FILE |

FIG. 9B

CONNECTION USER INFORMATION TABLE

| | |
|---|---|
| TERMINAL I.D. | 32 |
| PHONE NUMBER | |
| NAME | |
| TERMINAL ACTION MODE | |

FIG. 9C

SPOT DATA • • • n

| 33-1 | 33-2 |
|---|---|
| TIME STAMP | TIME STAMP |
| LATITUDE | LATITUDE |
| LONGITUDE | LONGITUDE |
| SATELLITE USED | SATELLITE USED |
| SPOT INDEX | SPOT INDEX |

FIG. 9D

| SATELLITE INFORMATION 34-1 | SATELLITE INFORMATION 34-2 |
|---|---|
| SATELLITE NUMBER | SATELLITE NUMBER |
| SATELLITE LOOK-UP ANGLE | SATELLITE LOOK-UP ANGLE |
| SATELLITE DIRECTIONAL ANGLE | SATELLITE DIRECTIONAL ANGLE |
| SATELLITE ELECTROMAGNETIC STRENGTH | SATELLITE ELECTROMAGNETIC STRENGTH |
| SATELLITE X COORDINATE | SATELLITE X COORDINATE |
| SATELLITE Y COORDINATE | SATELLITE Y COORDINATE |

FIG. 10

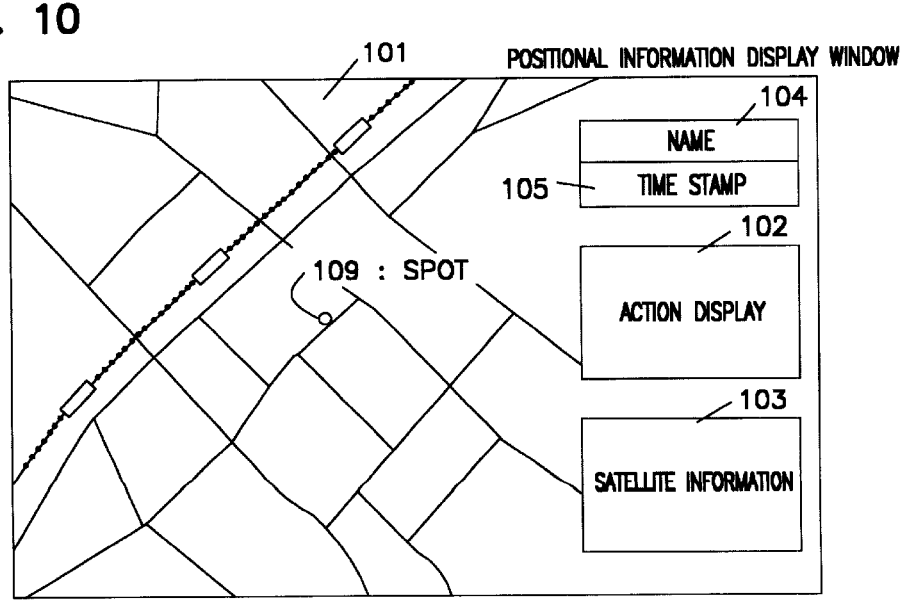

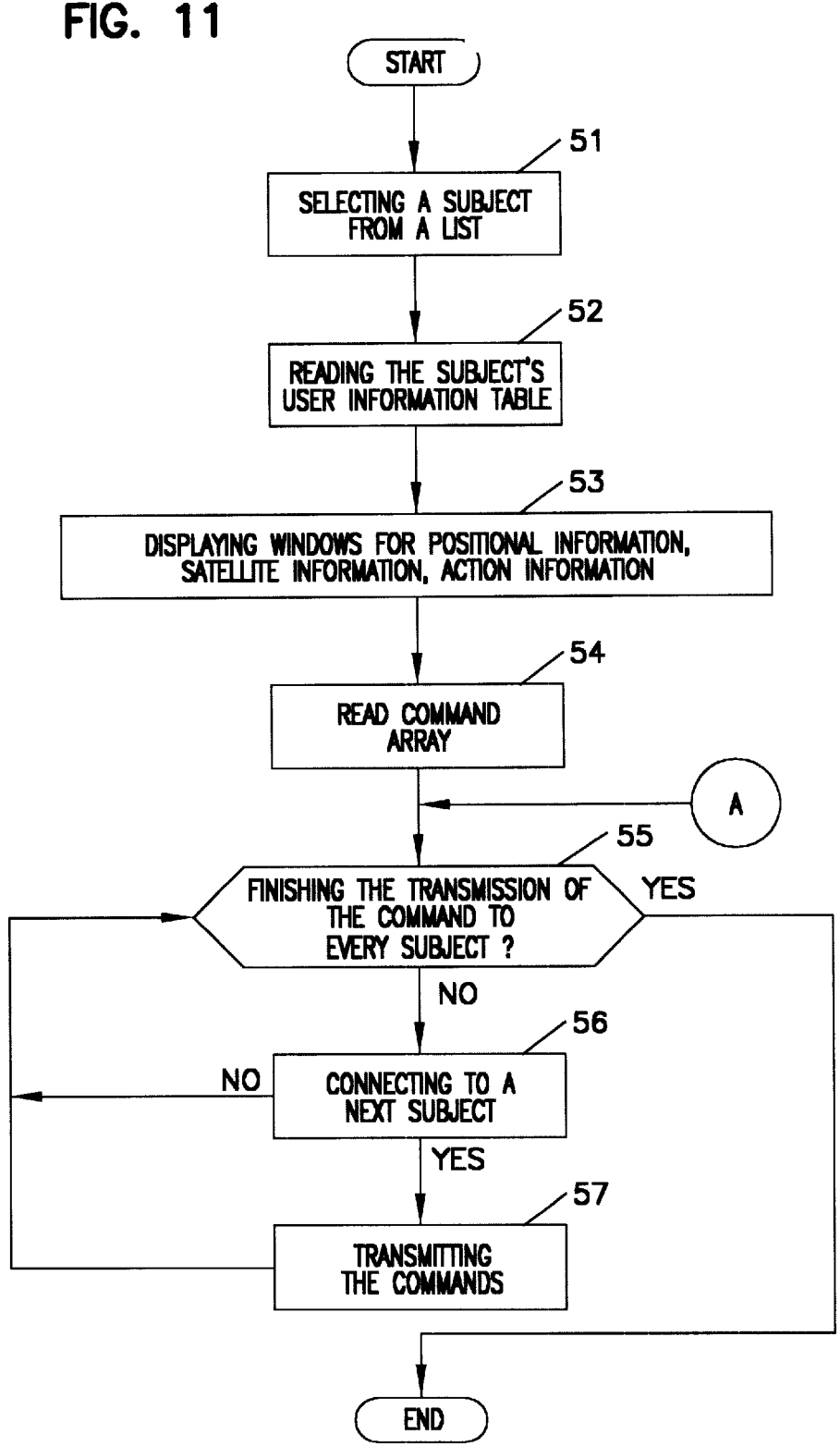

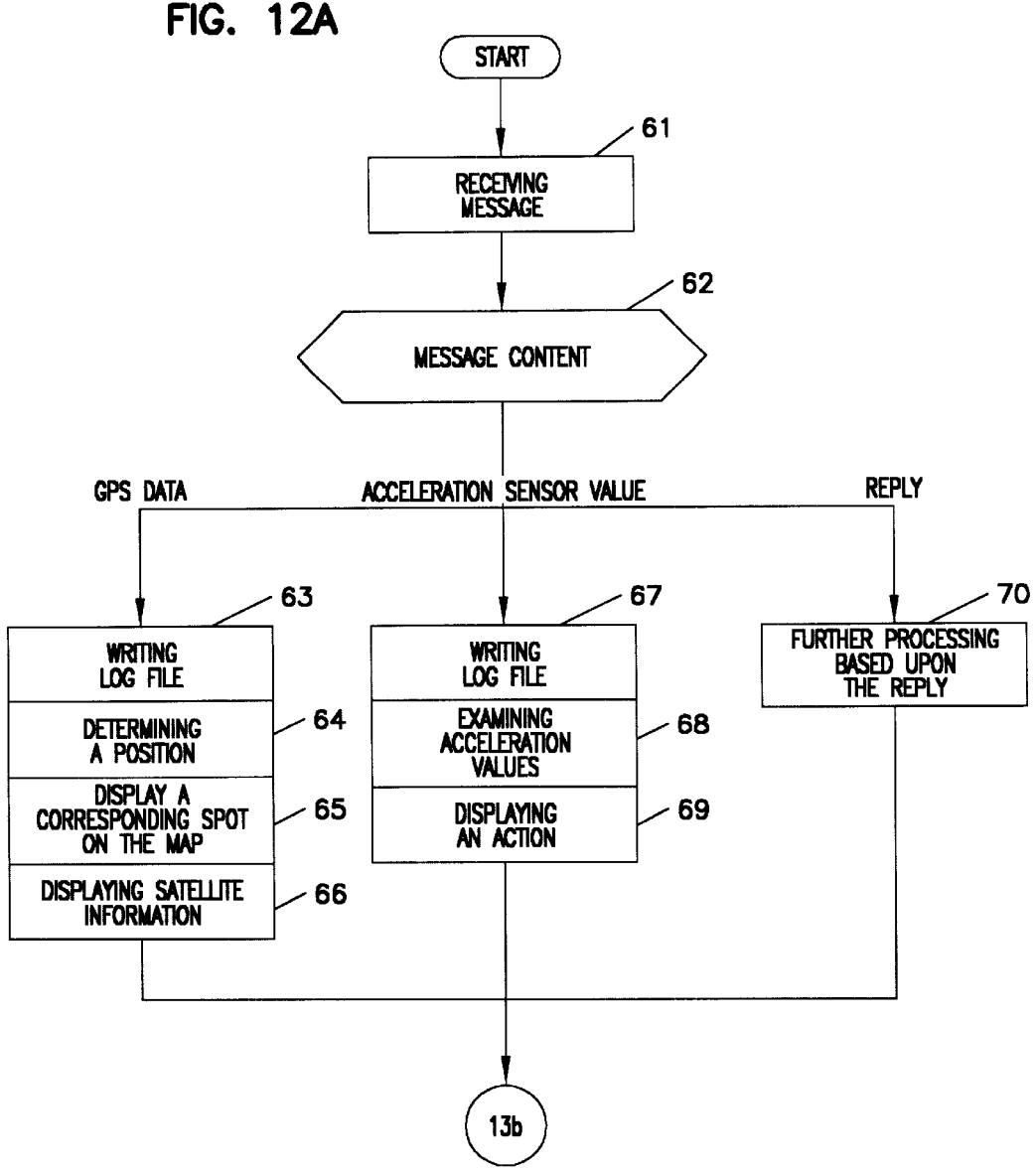

RESOURCE-SAVING EVENT-DRIVEN MONITORING SYSTEM AND METHOD

FIELD OF THE INVENTION

The current invention is generally related to an event-driven communication system, and more particularly related to a communication system that remotely monitors certain conditions and reports such conditions.

BACKGROUND OF THE INVENTION

The global positioning system (GPS) has been used to monitor the location of certain subjects including elderly wonderers. For example, Japanese Patent Laid Publication Hei 9-251069 discloses a system having a host unit for monitoring the location of a wonderer who wears a mobile communication unit. After the mobile communication unit receives the location data from the GPS, the host unit communicates with the mobile communication unit. The same prior art reference further discloses that the mobile communication unit obtains additional information such as vital sign including blood pressure and heart beat of the wearer and sends the information to the host unit. Another prior art reference, "A Recognition of Human Walking Motion by Using An Accelerometer," T.IEE Japan, Vol. 118-A No. 3, (1998) has disclosed the combined feature of detecting a type of human motion such as "standing," "walking" and "running" and reporting the detected motion to a host unit.

To conserve the resources in the monitoring system, Japanese Patent Laid Publication Hei 9-251069 also discloses that a host unit controls the frequency of transmission rate and the types of information from the mobile communication unit to the host unit by sending a control signal to the mobile unit. However, for example, this type of control is limited since the type of information necessary for monitoring a patient changes over a period of time and also depends upon the medical conditions of the patient. Although the mobile communication unit worn by a relatively healthy patient may not have to send any information other than positional information, once he had a heart attack, the information has to include medical conditions and has to be frequently sent to the host unit. In other words, the host cannot anticipate a necessary change in the control signal to the mobile communication unit without expending its resources on receiving continuously transmitted information and analyzing such information. In addition, resources in the host as well as the mobile communication unit are also inefficiently utilized when the positional data from the GPS is obtained. The host-terminal communication line is inefficiently kept active for a period during which the mobile communication unit waits for the GPS data.

To conserve resources in the monitoring system, each mobile communication unit and the host unit are desired to improve its communication efficiency.

SUMMARY OF THE INVENTION

In order to solve the above and other problems, according to a first aspect of the current invention, a method of notifying a host unit from a mobile communication unit, the mobile communication unit monitoring a subject with the mobile communication unit, including the acts of: placing the mobile communication unit in a predetermined inactive monitoring state; detecting at least one of a set of predetermined conditions with respect to the subject and generating a condition detection signal; placing the mobile communication unit in a predetermined active state in response to the condition detection signal; and initiating a first communication line with the host unit for transmitting the condition detection signal.

According to a second aspect of the current invention, a system for notifying certain conditions associated with a subject, comprising: a mobile communication unit for detecting at least one of a set of predetermined conditions in relation to a subject, the mobile communication being initially in a predetermined inactive monitoring state, upon detecting one of the predetermined conditions, the mobile communication unit generating a condition detection signal and changing its mode to a predetermined active state; and a host unit selectively in communication with the mobile communication unit for transmitting information between the mobile communication unit and the host unit, the mobile communication unit initiating a first communication line with the host unit for transmitting the condition detection signal.

These and various other advantages and features of novelty which characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

BRIEF DESCRIPTION OF THE DRAWINGS

FIG. 5 is a table illustrating exemplary commands and parameters that are used by the preferred embodiment of the event-driven monitoring system according to the current invention.

FIGS. 9A through 9D illustrate exemplary implementations of information tables.

FIG. 10 illustrates an output display monitor for displaying the satellite information and the associated information.

FIG. 11 is a flow chart illustrating acts involved in a preferred process of making a connection between a mobile communication unit and a host unit according to the current invention.

FIGS. 12A and 12B are flow charts illustrating acts involved in a preferred process of processing info received from a mobile communication unit according to the current invention.

DETAILED DESCRIPTION OF THE PREFERRED EMBODIMENT(S)

Figure 1:
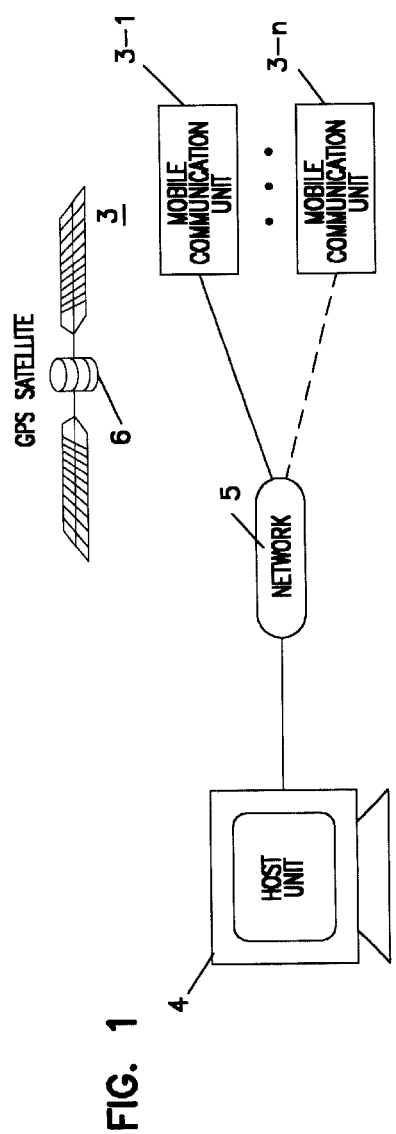
FIG. 1 is a block diagram illustrating one preferred embodiment of the event-driven monitoring system according to the current invention.

Referring now to the drawings, wherein like reference numerals designate corresponding structure throughout the views, and referring in particular to FIG. 1, a block diagram illustrates one preferred embodiment of the event-driven monitoring system according to the current invention. The preferred embodiment includes a host unit or a central unit 4 and at least one terminal unit 3 or mobile communication units 3-1 through 3-n, and the mobile communication units 3-1 through 3-n are independently capable of communicating with the host unit 4 via communication network 5 as well as a global positioning system (GPS) satellite 6 via satellite communication. Uniquely identifiable mobile communication units 3-1 through 3-n each obtain their present location via satellite communication by first making a position request to the GPS 6 and then receiving position data or GPS data from the GPS satellite 6. The uniquely identifiable mobile communications 3-1 through 3-n communicate with the host unit 4 via communication network 5 which include telephone networks, satellite communication, ISDN, radio communication and so on. The host unit 4 is generally located at a monitoring center where a predetermined number of subjects such as moving objects, animals or persons is registered for monitoring. The mobile communication units 3-1 through 3-n are generally at least portable or more desirably wearable by each of the subjects. In other words, the mobile communication units 3-1 through 3-n are powered by light-weight batteries, and the subjects are freely movable without being burdened by the mobile communication units 3-1 through 3-n.

Still referring to FIG. 1, in order to conserve the resources of the monitoring system, the preferred embodiment of the event-driven monitoring system according to the current invention substantially reduces an amount of wastefully active resources. In general, the mobile communication units 3-1 and 3-n are initially in a predetermined inactive or sleep mode where only specified resources are operating. Upon detecting one of a predetermined set of events for a given mobile communication unit, the mobile communication unit 3-1 wakens itself up or puts it in a predetermined active mode where the mobile communication unit is able to communicate with the host 4 and performs commands transmitted from the host unit 4. For example, to substantially reduce power consumption of the battery in the mobile communication unit 3-1, the mobile communication unit 3-1 monitors only heart rate in an inactive mode. In the same example, however, upon detecting the heart rate below a predetermined threshold value, the mobile communication unit 3-1 initiates communication with the host unit 4 and the GPS satellite 6 and transmits the monitored heart rate and the position of the mobile communication unit 3-1 to the host unit 4.

Figure 2:
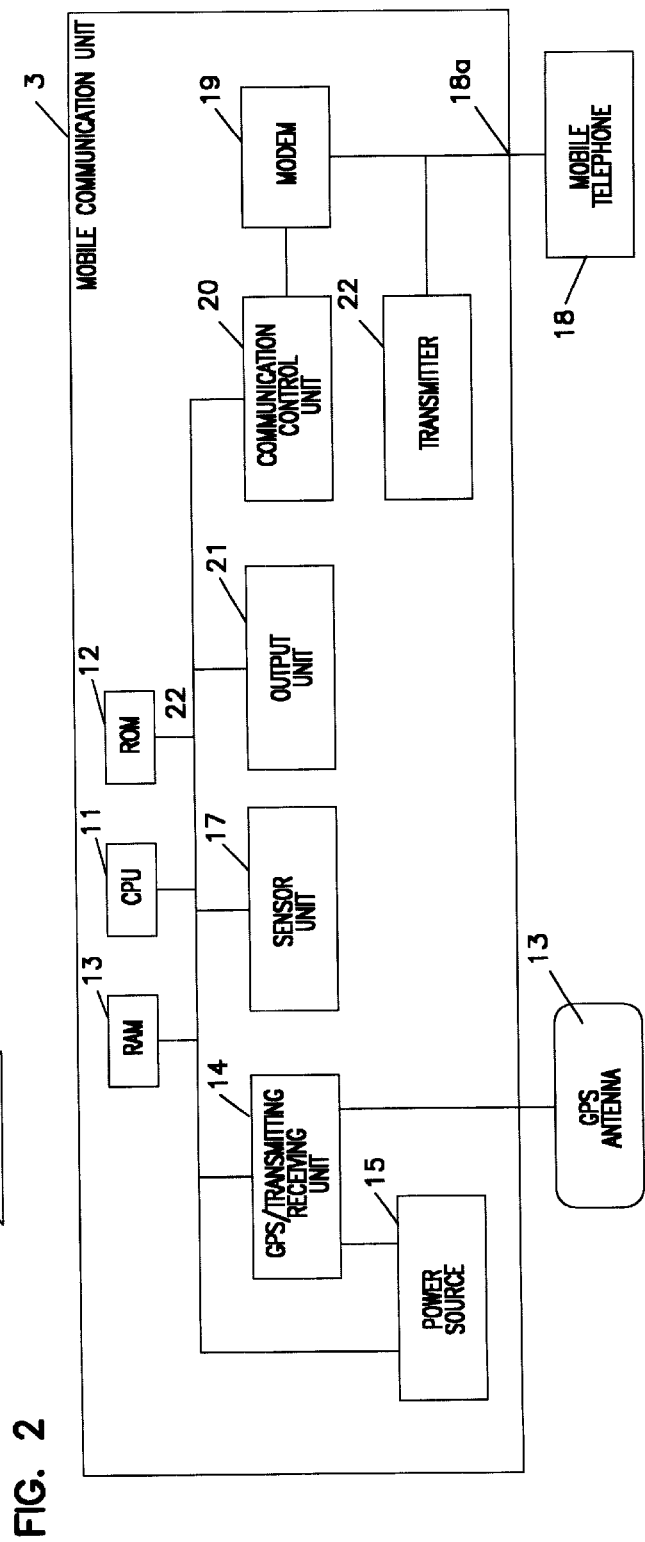
FIG. 2 is a block diagram illustrating one preferred embodiment of the mobile communication unit according to the current invention.

Referring to FIG. 2, one preferred embodiment of the mobile communication unit 3 is generally a self-contained unit. The mobile communication unit 3 has at least connection 18a to a cellular telephone 18 or a built-in transmission for establishing a network line with the host unit 4. The mobile communication unit 3 houses GPS-related components such as a GPS antenna 16 and a GPS transmitter/receiver 14 for communicating with the GPS satellite 6 via the GPS antenna 16. Similarly, the mobile communication unit 3 houses a modem 19 which is connected to the communication network connector 18a for converting certain analog signal to digital signal as well as a communication control unit 20 for controlling the connection of the communication network. In addition, the mobile communication unit 3 houses an output unit 21 such as an audio output unit and a display monitor for outputting information to the monitored subject. For example, the audio output unit outputs a predetermined warning sound or verbal warning. To monitor a predetermined set of events, the mobile communication unit 3 houses a corresponding set of sensors in a sensor unit 17. The above-described units are ultimately connected to processing components including a random access memory (RAM) unit 13, a central processing unit (CPU) unit 11 and a read-only memory (ROM) unit 12 so that the information is processed by the processing components. A power source 15 powers all of the above components possibly except for the modem 19 which can be powered by the cellular phone unit 18.

Still referring to FIG. 2, as described above, to conserve resources, certain units in the mobile communication unit 3 are not always activated. For example, the GPS-related units such as the GPS 14 is not activated until a GPS request command is issued by the CPU unit 11. Similarly, the communication control unit 20 and the modem 19 are also activated only when the communication with the host unit 4 is required. In general, a selected portion of the sensor unit 17 is generally active all the time during an inacitve mode or a sleep mode. Upon detecting a predetermined set of events, the sensor unit 17 generates a detection signal and sends it to the CPU unit 11 for further processing. Based upon the detection signal, the CPU unit 11 determines a response and activates other units for the response.

Figure 3:
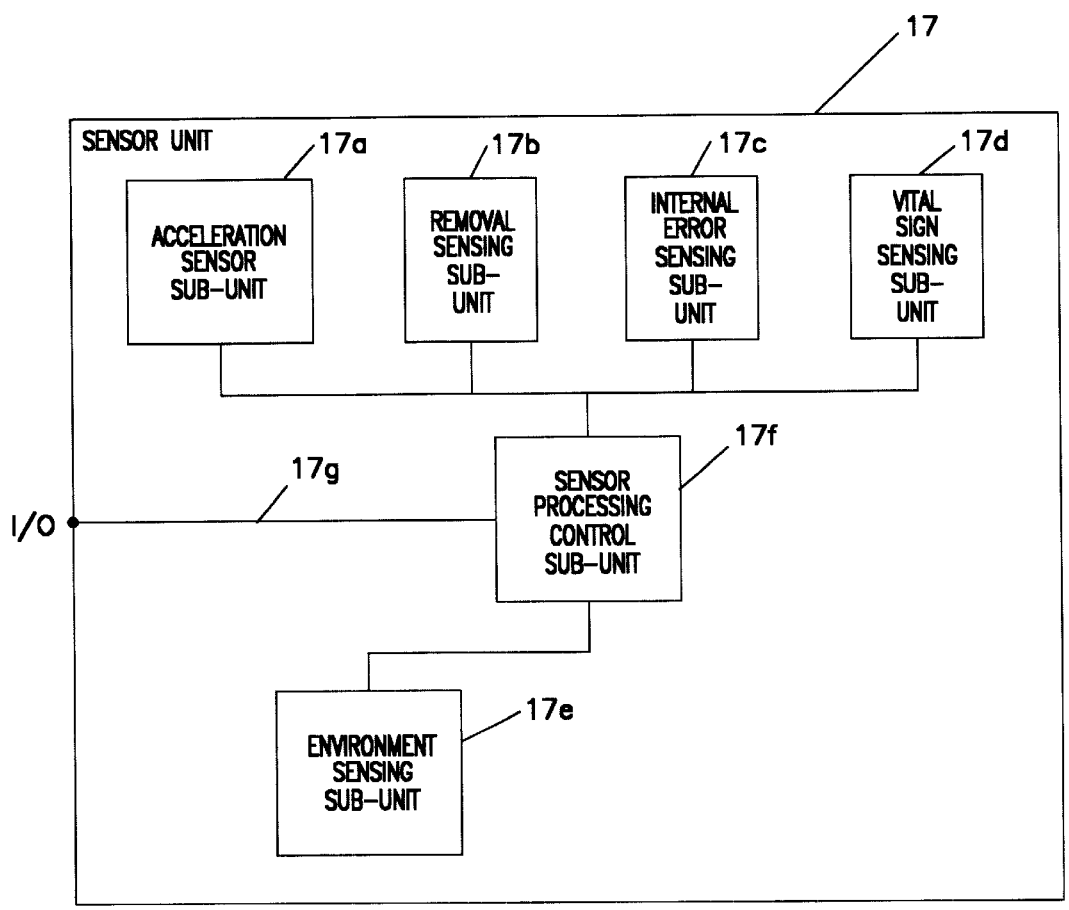
FIG. 3 illustrates one preferred embodiment of the sensor unit which is housed in the mobile communication unit according to the current invention.

FIG. 3 illustrates one preferred embodiment of the sensor unit 17, which is housed in the mobile communication unit 3 according to the current invention. The sensor unit 17 has a plurality of sensors which includes an acceleration sensing sub-unit 17-a for sensing movement of the mobile communication unit 3, a removal sensing sub-unit 17-b for detecting if the mobile communication unit 3 is still worn or carried by a monitored subject, an internal error sensing sub-unit 17-c for detecting a predetermined error or defect in the mobile communication unit 3, a vital sign sensing sub-unit 17-d for taking a predetermined set of vital signs, and an environmental sensing sub-unit 17-e for sensing a predetermined set of environment-related measurements.

The acceleration sensing sub-unit 17-a further includes an accelerometer for measuring the acceleration, and based upon a pattern of acceleration, the CPU unit 11 determines a motion type such as "standing still," "walking" or "running." The details of the motion determination have been disclosed in "A Recognition of Human Walking Motion by Using An Accelerometer," T.IEE Japan, Vol. 118-A No. 3, (1998), and the reference is hereby incorporated by reference. One implementation of the removal sensing sub-unit 17-b is a micro switch that is kept closed while the subject wears the mobile communication unit 3. In the alternative, the removal sensing sub-unit 17-b can be implemented as a part of the acceleration sensing sub-unit 17-a for determining the lack of movement for a predetermined time or a part of the vital sign sensing sub-unit 17-d for detecting the lack of any vital sign for a predetermined time or a combination thereof. The internal error sensing unit sub-unit 17-c is a diagnostic software module for analyzing the status of sensors. If any malfunction is detected for a sensor, a corresponding sensor malfunction signal is generated. The vital sign sensing sub-unit 17-d further includes components for measuring a certain set of vital signs such as blood pressure, heart rate, body temperature and so on. Each of these vital signs is monitored by a particular sensing device which may be directly in contact with the subject. The environment sensing sub-unit 17-e measures predetermined environmental conditions such as temperature, humidity and so on. Each of these environmental conditions is measured by a particular measuring device. A sensor processing control sub-unit 17-f coordinates input and output (I/O) among the above-described sensing sub-units 17-a through 17-f and also handles I/O with other units in the mobile communication unit 3 through an I/O port 17-g.

Figure 4:
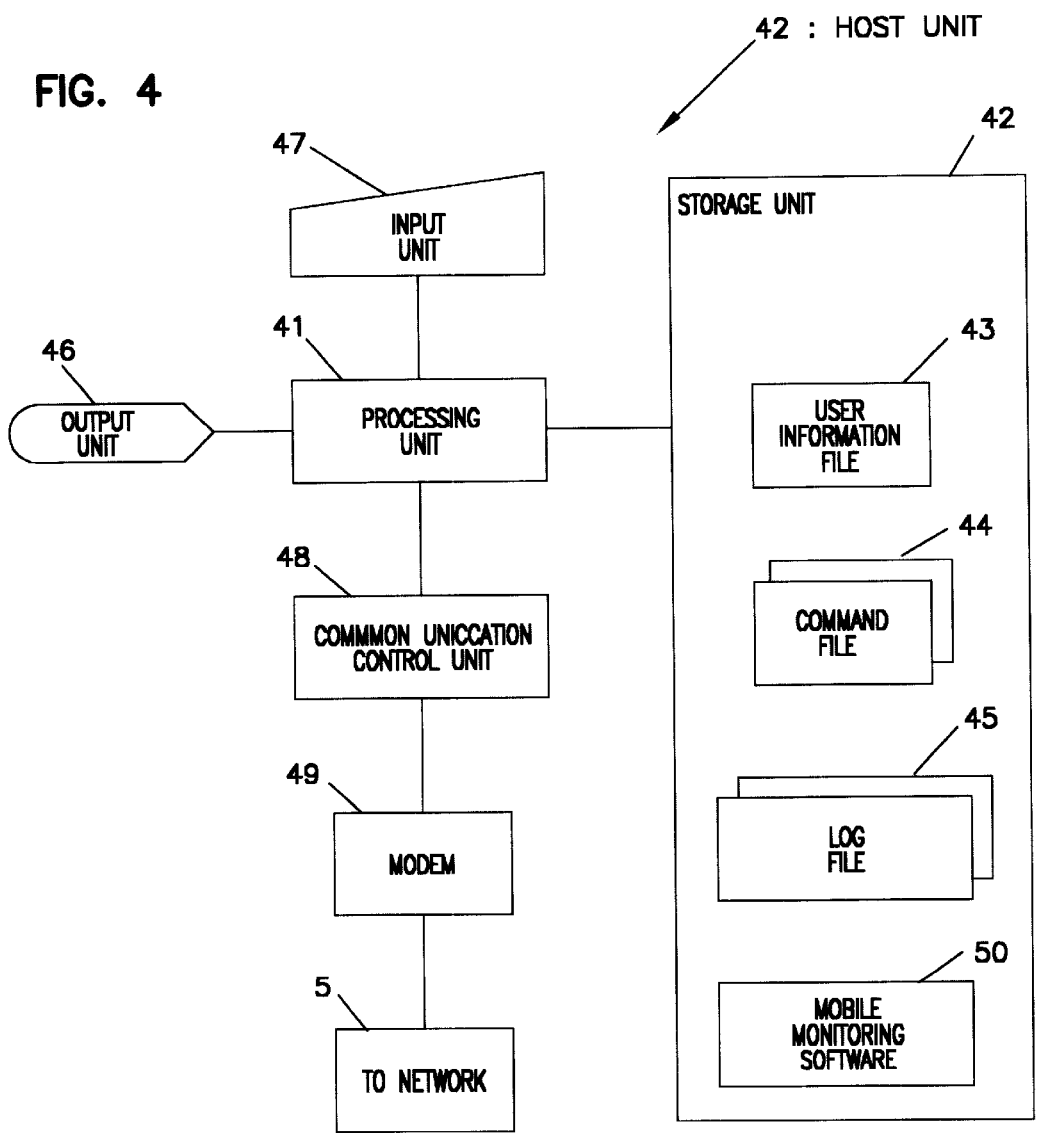
FIG. 4 is a block diagram illustrating one preferred embodiment of the host unit according to the current invention.

Now referring to FIG. 4, the host unit 4 is connected to a communication network 5 and generally includes application software, data and processing hardware.

The hardware includes communication hardware, a processor and I/O hardware. The communication hardware further includes a modem 49 which is connected to the communication network 5 for converting certain analog signal to digital signal as well as a communication control unit 48 for controlling the connection of the communication network. A processing unit 41 including a primary memory and a central processing unit (CPU) processes the information to and from the communication network 5. An input unit 47 such as a mouse and a keyboard is also connected to the processing unit 41 to input commands for monitoring the subjects. For example, the commands specify a subject to be monitored as well as a kind of his or her vital sign. An output unit 46 such as a display monitor is connected to the processing unit 41 to display the information on the monitored subjects. The displayed information includes the position of the monitored subject on a map as well as other information associated with the subject.

Still referring to FIG. 4, the host unit 4 also includes a memory storage unit 42. In the memory storage unit 42, information related to monitoring the subjects is organized in at least three types of files for each subject. A user information file 43 stores user-related information for each subject including an identification number for a mobile communication unit 3 as shown in FIG. 1, a telephone number of the mobile communication unit 3 and a name of the subject. The user information file 43 also stores a file name of an event-driven file or a set of predetermined events to be detected by the mobile communication unit 3. Upon detecting one of these predetermined events, the mobile communication unit 3 initiates communication with the host unit 4. A command file 44 includes an array of commands to be transmitted to the mobile communication unit 3 so that the mobile communication unit 3 locally executes the commands in an efficient manner. A log file 45 logs information on the position of the subject and other information associated with the monitored subject. The memory storage unit 42 also stores an application program 50 for coordinating resources in monitoring the subjects.

The monitoring application program 50 is read into the primary memory of the processing unit 41, and it reads data of a specified subject from the user information file 43 as well as the command file 44. The monitoring application program 50 transmits the commands to a corresponding one of the mobile communication units 3-1 through 3-n based upon the user-related information via communication network 5. The monitoring application program 50 also receives information from one of the mobile communication units 3-1 through 3-n via communication network 5 when any of the mobile communication units 3-1 through 3-n detects one of the predetermined events.

Now referring to FIG. 5, a table illustrates exemplary commands and parameters that are used by the preferred embodiment of the event-driven monitoring system according to the current invention. The following commands are related to the command execution. "Command Array Register Start" sets the mobile communication unit 3 in a command array registering mode. Following the above command until "Command Array Register End," any command is stored in an array of commands, and these stored command are executed when "Command Array Execution Start" is issued. "Command Array Execution End" terminates the command array execution and switches the command mode of the mobile communication unit 3 to an immediate execution mode. "Command Array Register End" also switches the command mode of the mobile communication unit 3 to the immediate execution mode.

Still referring to FIG. 5, the following commands are related to communication. The mobile communication unit 3 initiates a predetermined communication line with the host unit 4 upon receiving "Connect Communication Line" and terminates the communication line upon receiving "Disconnect Communication Line." In attempt to establish the communication line, the mobile communication unit dials a predetermined number of redialing as specified in "# of redials" with a predetermined interval as specified in "redial interval." "Rest" suspends processing of the mobile communication unit 3 for a predetermined amount of time as specified in an associated parameter.

The GPS-related commands include the following. "GPS Power On" and "GPS Power Off" controls the power to the GPS units. "GPS Data Read" enables the GPS receiver 14 to read the GPS data from the GPS satellite 6 and to transmit the GPS data to the host unit 4. The beginning of the GPS data is marked by a word contained in the parameter "start keyword." "# of characters" specifies the number of characters in the "start keyword" parameter while "# of lines" specifies a number of lines to be read in the GPS data following the keyword. The "Position Result" command determines if GPS measurement is "measurement available," "measurement not available" or "no response" based upon the length of the GPS data following a predetermined GPS data keyword. If the length does not exceed a predetermined threshold value, after a predetermined period of "time-out period," "measurement not available" is returned. Similarly, "measurement not available" is also returned if no GPS data keyword is detected after a predetermined period of "no response period." Lastly, the command "Connect After Position Result" establishes a communication line based upon the GPS position result. The parameters for the "Connect After Position Result" command are the same as those for the "Position Result" and "Connect Communication Line" commands.

The rest of commands is related to event-driven features. The following commands are issued by a host unit 4 to a mobile communication unit 3. In the alternative, the mobile communication unit 3 also executes the following commands without the involvement of the host unit 4. The command "Acceleration Sensor Read" obtains acceleration values from an acceleration sub-unit 17-a as shown in FIG. 3 and transmits the data to the host unit 4. A number of values sampled is specified by "# of samples" while the sample interval is specified by "sample interval" in milliseconds. The "Output" command outputs a set of characters or sound specified in "text output." The "Event Recognition Output" command causes the mobile communication unit 3 to determine whether or not any of the predetermined actions or events has transpired based upon the data gathered by the sensor unit 17. For example, based upon the acceleration values, the CPU 11 determines whether the action is one of the predetermined events or actions. If "walking" is one of the predetermined actions and the acceleration values indicate walking, the mobile communication unit 3 establishes a communication line with the host unit 4 and transmits the information. The "Specific Event Recognition" commands specifies a particular action or event in "action/event" parameter, and the mobile communication unit 3 determines whether or not that specific event has transpired in a predetermined period as stored in "time-out period." If the specified action or event indeed takes place, the mobile communication unit 3 transmits the information. The "action/event" parameter can hold more than one action or event, and when one or more of the specified actions or events is detected, the mobile communication unit reports the host unit 4. Additionally, the "Connect After Specific Event Recognition" command initiates a communication line with the host unit 4 after a specific action or event is detected. The parameters for the "Connect After Specific Event Recognition" command are the same as those for the "Specific Event Recognition" and "Connect Communication Line" commands. The above-described commands are merely illustrative and not exhaustive for the preferred embodiment. The above-described parameters for the commands are also merely illustrative.

Figure 6:
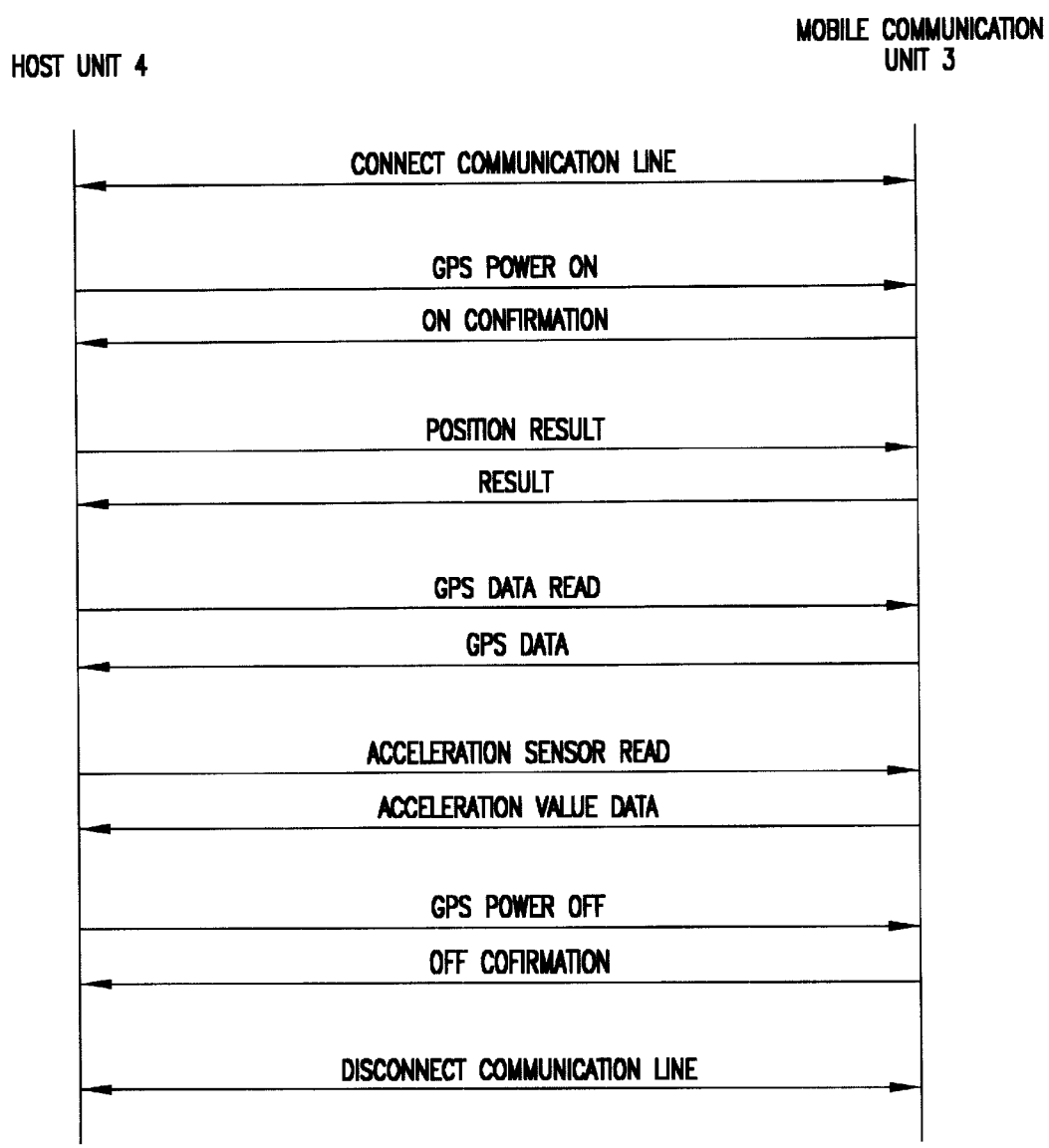
FIG. 6 is an exemplary sequence of commands for communicating between a host unit and a mobile communication unit for the GPS position and a specific action/event determination.

Now referring to FIG. 6, an exemplary sequence of commands is illustrated for communication between a host unit 4 and a mobile communication unit 3 regarding the GPS position and a specific action/event determination. Time line progresses from the top to the bottom of the diagram. The host unit 4 issues the "Connect Communication Line" command to the mobile communication unit 3, and the communication line is established as indicated by a line with double arrow heads. After the host unit 4 issues the "GPS Power On" command, and the mobile communication unit 3 returns an On confirmation signal, the host unit 4 issues the "Position Result" to ascertain whether or not the GPS Data is available as returned in the result signal. When valid GPS data is available, the GPS data is transmitted to the host unit 4 from the mobile communication unit 3 in response to the "GPS Data Read" command. Furthermore, the mobile communication unit 3 transmits the acceleration value data to the host unit 4 in response to the "Acceleration Sensor Read" command. After the above-described information transfer is completed, the host unit 4 turns off the GPS power source via the "GPS Power Off" command. When the power off is confirmed by an off confirmation signal from the mobile communication unit 3, the host unit 4 initiates to disconnect the communication line. In the above sequence, the communication to the GPS satellite 6 is maintained for updating the GPS data. However, the "GPS Power Off" command may be issued immediately after the "GPS Data Read" command to conserve the resources in the system according to the current invention.

Figure 7:
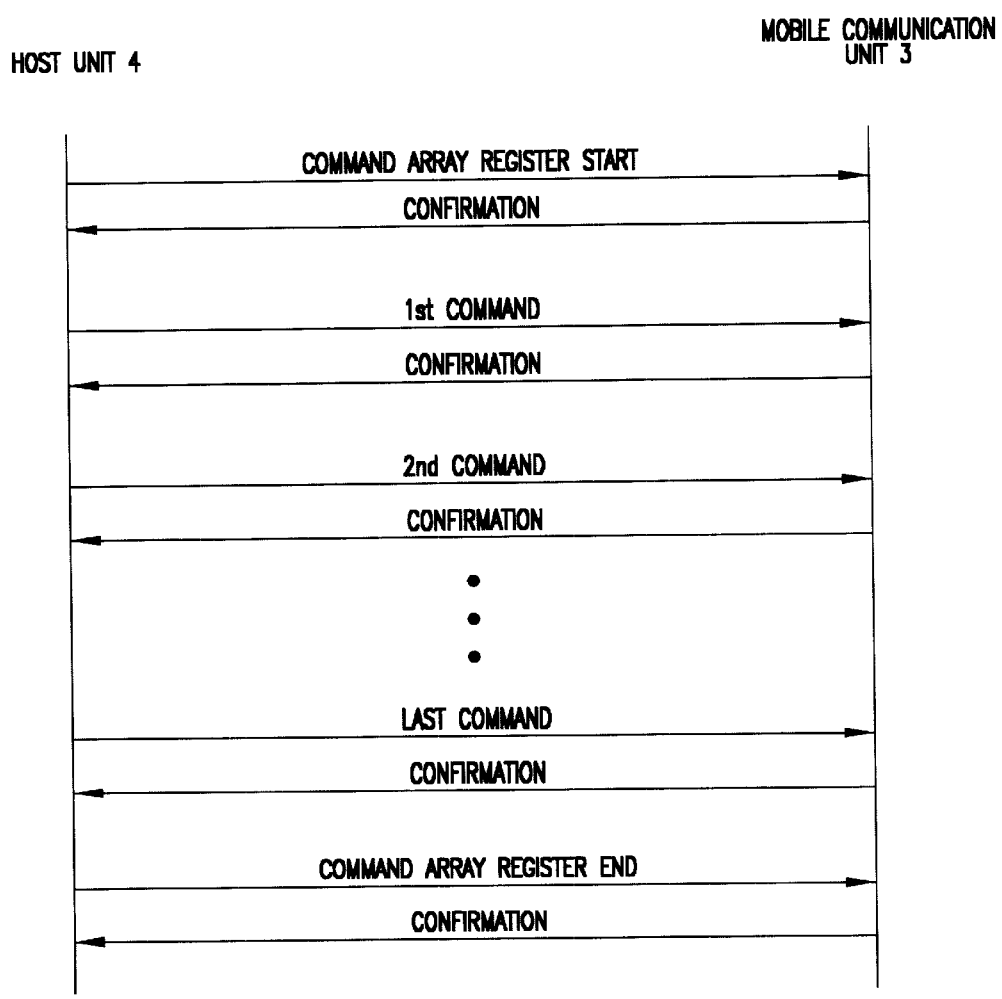
FIG. 7 is another exemplary sequence of commands for registering an array of commands.

Now referring to FIG. 7, another exemplary sequence of commands is illustrated for registering an array of commands at a RAM unit 13 in a mobile communication unit 3 of FIG. 2. Time line progresses from the top to the bottom of the diagram. Assuming that the host unit 4 and the mobile communication unit 3 have an already established communication line, the host unit 4 indicates the start of registering an array of commands for later execution by transmitting the "Command Array Register Start" command to the mobile communication unit 3 so that the command execution mode of the mobile communication unit 3 is altered from immediate execution to delayed execution (command array registration mode). After an initial confirmation signal is received, the host unit 4 sends a series of commands to the mobile communication unit 3 following an individual confirmation signal. Each command is stored in the RAM unit 13 of the mobile communication unit 3. Subsequent to the last command, the host unit 4 indicates the end of the command registration by the "Command Array Register End" command. At this time, the mobile communication unit 3 resumes the immediate command execution mode.

Figure 8:
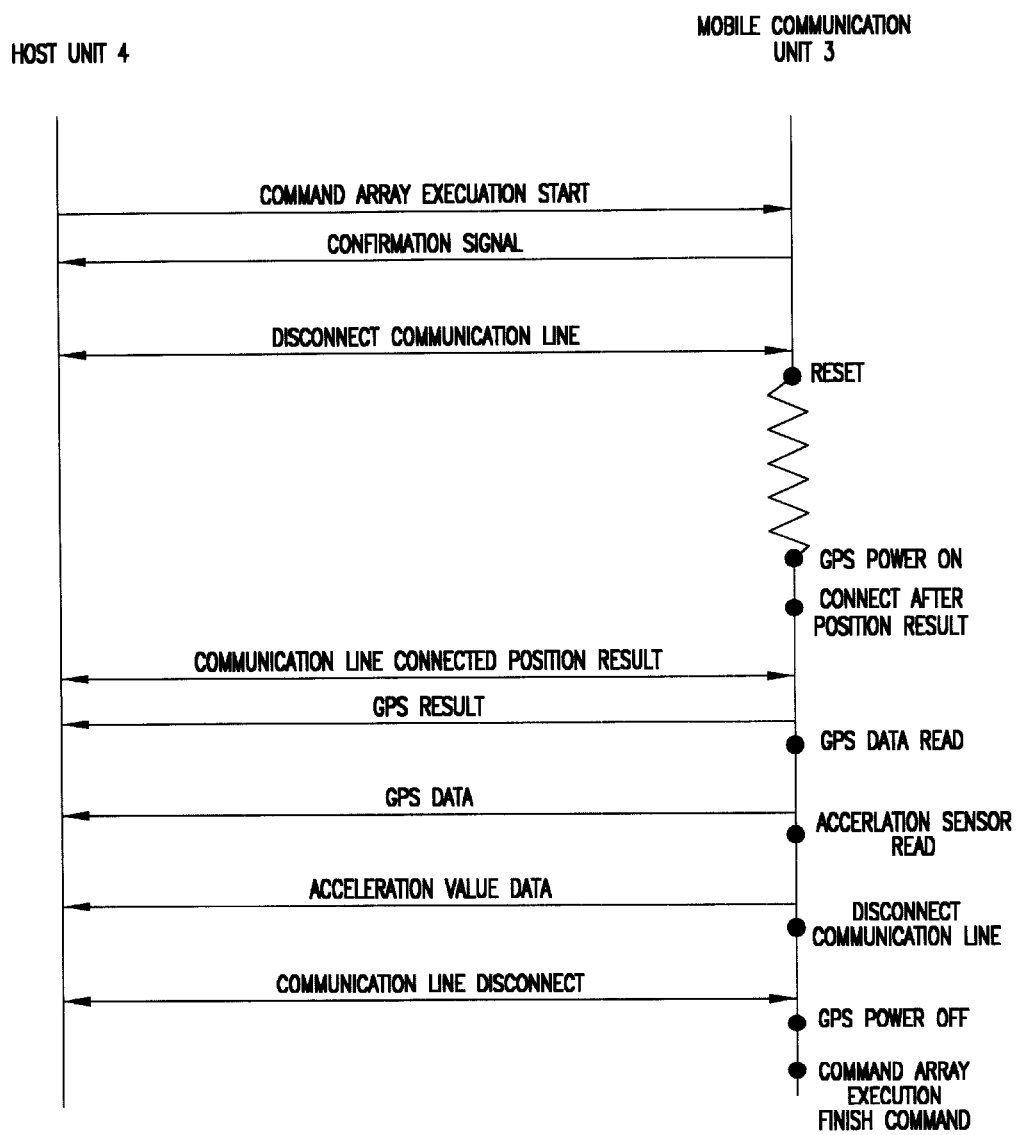
FIG. 8 is yet another exemplary sequence of commands for executing an array of commands stored at a mobile communication unit.

Now referring to FIG. 8, yet another exemplary sequence of commands is illustrated for executing an array of commands stored at a mobile communication unit 3. Time line progresses from the top to the bottom of the diagram. Dark dots on the time line for the mobile communication unit each indicate the execution of a command stored in an array. After the host unit 4 indicates the start of the array command execution by the "Command Array Execution Start" command and its confirmation signal from the mobile communication unit 3, the communication line between the host unit 4 and the mobile communication unit 3 is disconnected to conserve communication resources. For a predetermined amount of time, the mobile communication unit 3 suspends its processing according to the "Rest" command. The mobile communication unit 3 activates the GPS unit according to the "GPS Power On" command. Assuming that the GPS data is available, the "Connect After Position Result" command reconnects the communication line between the host unit 4 and the mobile communication unit 3, and the GPS result is transmitted to the host unit 4. The mobile communication unit 3 then executes the "GPS Data Read" command, and the GPS data is transmitted to the host unit 4. Similarly, the mobile communication unit 4 executes the "Acceleration Sensor Read" command so that the acceleration value data is transmitted to the host unit 4. The communication line is disconnected by the "Disconnect Communication Line" command, and the GPS unit is shut off by the "GPS Power Off" command. Lastly, at the end of the command array execution, the command execution mode is changed to the immediate execution mode by the "Command Array Execution Finish" command. Preferably, in order to improve the efficient use of the communication line, the "Command Array Execution Start" command should be issued immediately after an array of commands is registered using the same communication line.

FIGS. 9A through 9D illustrate exemplary implementations of information tables. Now referring particular to FIG. 9A, one exemplary implementation of the user information file as shown in FIG. 4 is a user-info table. A separate user-info table 31 is allocated for each subject and includes entries such as a command array transmit flag, a command array transmit error flag, a terminal ID, a phone number, a name, a spot data pointer, # of satellites, a satellite information pointer, action info, an acceleration sensor correction value and a predetermined event/action file. The command array transmit flag is initiated to zero, and when the command array is transmitted in a normal manner, the value is changed to one. The command array transmit error flag is initiated to zero, and when an error is detected in transmitting the command array commands, the value is changed to one. The terminal ID is an identification number for identifying a mobile communication unit 3 for the subject. The phone number is for the portable telephone 18, which is used in connection with the mobile communication unit 3. The name refers to the subject's name. The spot data pointer points to a beginning memory address where sampled position data is stored. # of satellites indicates a number of satellites that the mobile communication unit 3 has access, and the number generally ranges from eight to twelve. The satellite information pointer points to a beginning memory address where information on the above satellites is stored. The action information stores the latest recognized action of the subject. The acceleration sensor correction value specifies a predetermined value for correcting sampled acceleration values. The predetermined event/action file contains information on events and actions to be detected by the mobile communication unit 3.

Referring to FIG. 9B, one exemplary implementation of a connection user info table 32 is illustrated. The connection user info table 32 resides in the processing unit 41 and contains duplicate information on the terminal ID, the phone number and the name. The connection user info further includes an entry on a terminal action mode which specifies either immediate or delayed command execution.

Referring to FIG. 9C, one exemplary implementation of the sampled position data format is illustrated. Each of the tables 33-1 and 33-2 contains a set of predetermined information for one sampled position, and these tables are chronologically grouped together for the same subject. Each of the tables 33-1 and 33-2 includes entries such as a time stamp for indicating the sampled time, a latitudinal value of the sampled position, a longitudinal value of the sampled position, a number of used satellites and the spot index for identifying the spot data.

Referring to FIG. 9D, one exemplary implementation of a satellite info table 34 is illustrated. Separate satellite info tables such as 34-1 and 34-2 are allocated for each satellite and resides in the processing unit 41. Each satellite info table 34 contains a satellite number, a satellite look-up angle, satellite directional angle, satellite electromagnetic strength, a satellite x coordinate and a satellite y coordinate. The satellite x and y coordinates are determined based upon the above angular information.

FIG. 10 illustrates an output display monitor for displaying the satellite information and the associated information. A display window 101 shows a map and a spot or a sampled position 109 in the map. The display window 101 also contains additional sub-windows for displaying a monitored subject's name in a first sub-window 104, a sample time in a second sub-window 105, a current action in a third sub-window 102 and the satellite information in a fourth sub-window. The current action is indicated by an icon which illustrates walking, running or falling.

Referring to FIG. 11, a flow chart illustrates acts involved in a preferred process of making a connection between a mobile communication unit and a host unit according to the current invention. Some of the following acts are described in relation to the preferred embodiment as illustrated in FIGS. 4, 9 and 10. When a subject is or subjects are selected via the input unit 47 in act 51, the mobile monitoring software 50 reads the subject's name from the user information file 43 and displays it on the output unit 46. In act 52, the associated user information is read into the memory, and the information is initialized. In act 53, sub-windows 102–105 display the positional information, the satellite information and the action information in the output unit 46. Commands are read into memory from the command file 44 in order to transmit them to a mobile communication unit 3 of one of the selected subjects in act 54. If it is determined by examining the command array transmit flag and the command array transmit error flag that the commands have been transmitted to every mobile communication unit 3 of the selected subject(s) in act 55, the preferred process ends. On the other hand, if it is determined that the commands have not been transmitted to every mobile communication unit 3 of the selected subject(s) in the act 55, the terminal ID, the phone number and the name of the user info table 31 are copied to the connection user info table 32. The terminal action mode is set to immediate execution, and a communication line is connected to the mobile communication unit 3 in act 56 so as to transmit the commands to the mobile communication unit in act 57. In order to establish the communication line, if the communication line is not established after a predetermined number of redial attempts, the transmit error flag is set to one and an error message is displayed on the output unit 46. Consequently, the preferred process returns to act 55 upon experiencing the error.

Figure 12B:
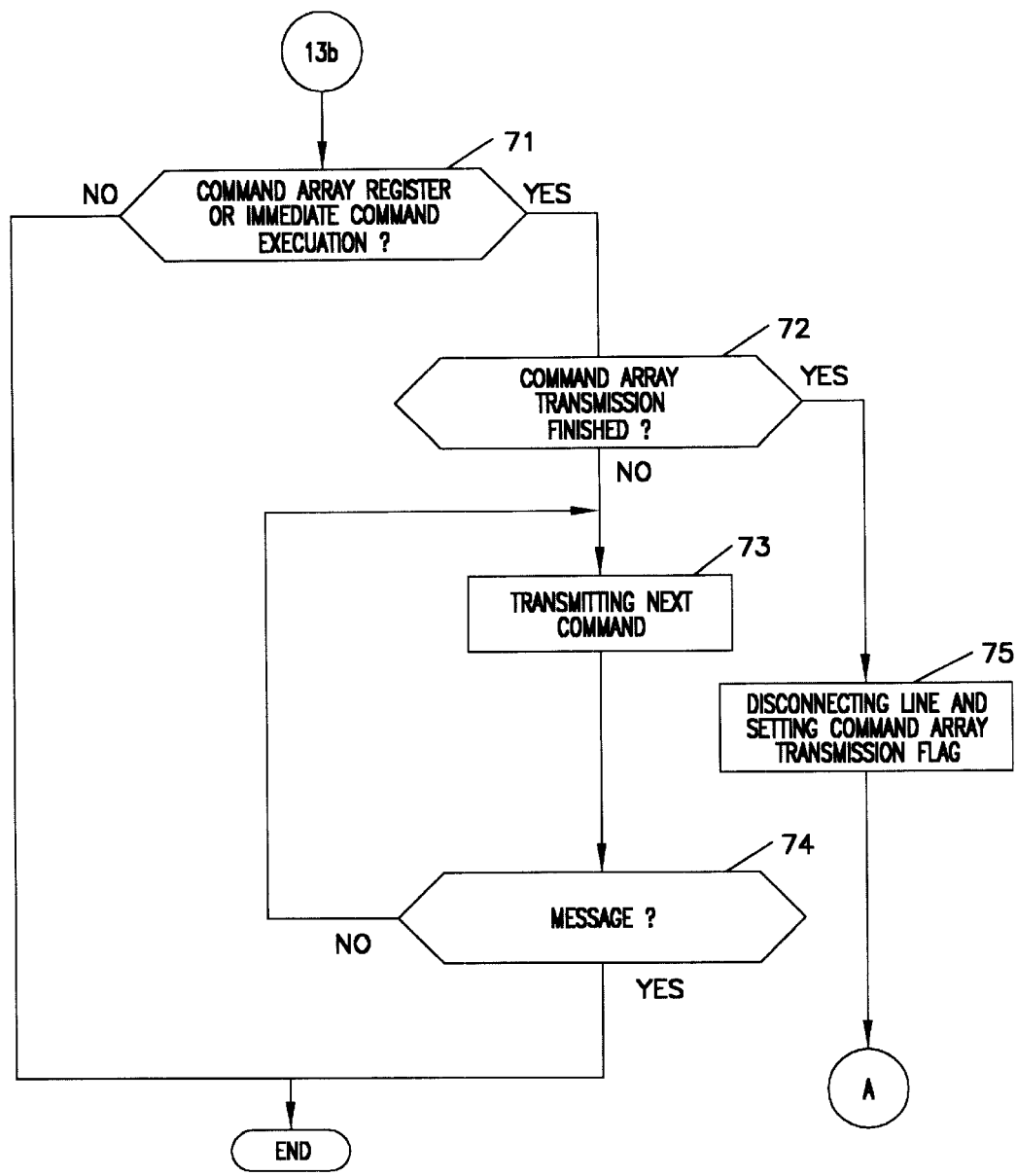

Referring to FIGS. 12A and 12B, flow charts illustrate acts involved in a preferred process of processing information received from a mobile communication unit according to the current invention. Some of the following acts are described in relation to the preferred embodiment as illustrated in FIGS. 4, 9 and 10. Upon receiving an information signal or a message from the mobile communication unit 3 in act 61, the information signal is examined in act 62 to perform a different set of acts. In case the received information is GPS data in response to the GPS Read command, the received GPS data is written into a log file 45 as a record in act 63. In act 64, if a received portion of the GPS data includes positional information, the positional information is then written to a next available block in the memory area whose beginning address is pointed by the spot data pointer in the user info table 31. Based upon the positional information of the GPS data, display coordinates for the sampled spot are determined also in act 64. The sampled spot is displayed in the map window 101 in act 65. Lastly, in this branch of processing, if the GPS data includes the satellite information, the satellite information is written to a next available block in the memory area whose beginning address is pointed by the satellite information pointer in the user info table 31. Based upon the satellite information, the satellite coordinates are determined for displaying in the window 103 along with the satellite number and satellite electromagnetic strength in act 66.

Still referring to FIG. 12A, in case the received information is an acceleration sensor value in response to the Acceleration Sensor Read command, the acceleration value is written into a log file 45 as a record in act 67. The acceleration value is then copied to an array of the acceleration values in act 68. Based upon the array of the acceleration values, an action of the corresponding subject is determined, and the action is stored in the action info entry of the user info table 31 in act 69. In the act 69, the action is further displayed by an icon in the display window 102. The certain action is associated with a sound generation act. In the alternative process, the above-described acts 67, 68 and 69 are performed by a mobile communication unit 3, and the host unit 4 only displays the processed information.

Lastly, in case the received information is a reply or a return code in response to the executed command, a corresponding set of acts is performed in act 70. If a normal or error-free code is returned after the "Command Array Register Start" command, the terminal action mode of the connection user info table 32 is set to the delayed execution mode (the command array registration mode). Subsequently, if an error-free code is returned after the "Command Array Register End" command, the terminal action mode of the connection user info table 32 is set to the immediate execution mode. On the other hand, if a return code is an error, the transmit error flag is set to one, an error message is displayed in the output unit 46, and the process goes to act 55 of FIG. 11 where indicated by a circled capital letter A. Similarly, in response to the commands, "Command Array Register Start," "Command Array Register End" and "Command Array Execute," if an error code is returned, the transmit error flag is set one, an error message is displayed in the output unit 46, and the process goes to act 55 of FIG. 11. If a mobile communication unit 3 is in the immediate execution mode or in the command array execution mode, and an abnormal return code other than the above mentioned one is received, the process proceeds to a next act after an error message is displayed in the output unit 46.

Referring to FIG. 12B, continuing from the flow char of FIG. 12A, in act 71, it is determined whether or not the terminal action mode is the immediate execution mode. If the terminal execution mode is neither in the command array register mode nor the immediate command execution mode, the preferred process ends. On the other hand, the terminal execution mode is either the command array register mode or the immediate command execution mode, it is further determined in act 72 whether or not a command array has been transmitted and the command array transmit flag in the user info table 31 is zero. If both of the conditions are met in the act 72, the communication line between the host unit 4 and the mobile communication unit 3 is disconnected, and the log file 45 is closed in act 75. Furthermore, in the act 75, the command array transmit flag in the user info table 31 is set to one, and the process goes to act 55 of FIG. 11 where indicated by a circled capital letter A. If, on the other hand, any command is not yet transmitted from the command array in the act 72, a next command is transmitted in act 73. If there is a return message, it is processed. If there is no return message, then the process returns to the act 73.

Figure 13:
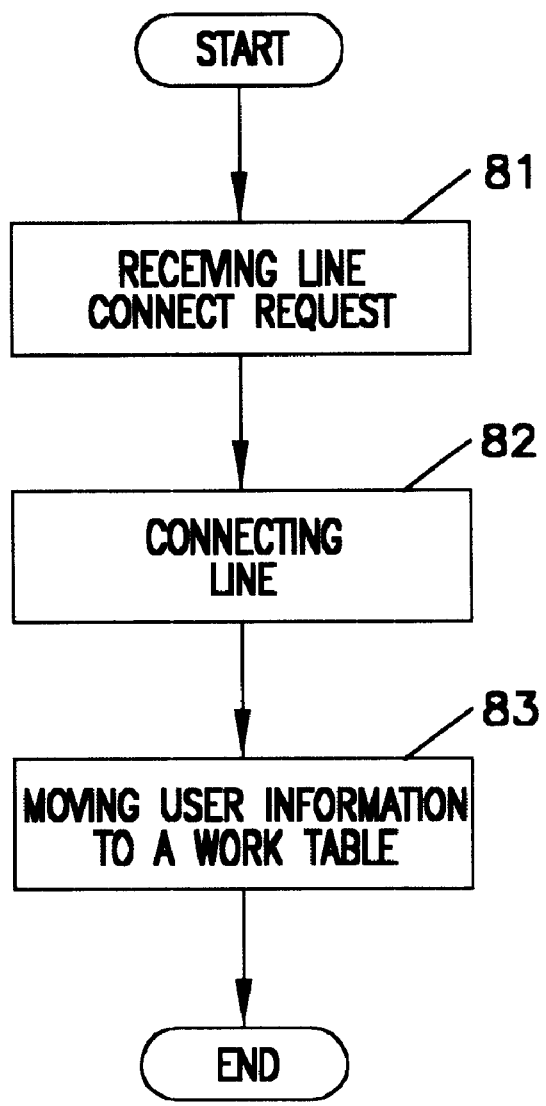
FIG. 13 is a flow chart illustrating acts involved in a preferred process of making a connection to a host based upon a request from a mobile communication unit according to the current invention.

Referring to FIG. 13, a flow chart illustrates acts involved in a preferred process of making a connection to a host based upon a request from a mobile communication unit according to the current invention. The following acts are described in relation to the preferred embodiment as illustrated in FIGS. 1, 4 and 9. The mobile communication unit 3 sends a connection request to the host unit 4 in order to establish a communication link between the two units. The host unit 4 receives the communication request signal in act 81, and the monitoring software 50 processes the communication request in act 82. In order to establish the communication link, the monitoring software 50 duplicates information from the user info table 31 in the connection user info table 32 in act 83. The connection user info table 32 resides in the processing unit 41, and the duplicated information includes the terminal ID, the phone number and the name. The connection user info further includes an entry on a terminal action mode which is now set to the command array immediate execution mode. A corresponding log file 45 is now opened as well, and an appropriate message is displayed on an output unit 46.

After the connection, for example, the monitoring software 50 on the host unit 4 transmits an array of commands to the mobile communication unit 3 of each of the selected monitoring subjects. In response to the commands, the host unit 4 receives information such as the GPS data and the action information. Then, the host unit 4 stores these information in a user info table 31, a spot data table 33 and a satellite info table 34. The host unit 4 further displays the information in display windows including a map window 101, an action window 102 and a satellite info window 103. A plurality of the spot data sets for the same subject can be displayed on the map window 101 as multiple spots 109 to indicate a moving path. This feature is used for emergency to track a subject on real time. Based upon the movement path and the action, the host unit 4 further transmits the Output command for causing the mobile communication unit 4 to generate a warning sound or an audio help message. Alternatively, the Output command can specify a visual alert signal such as a blinking lamp on the mobile communication unit 3.

Figure 14:
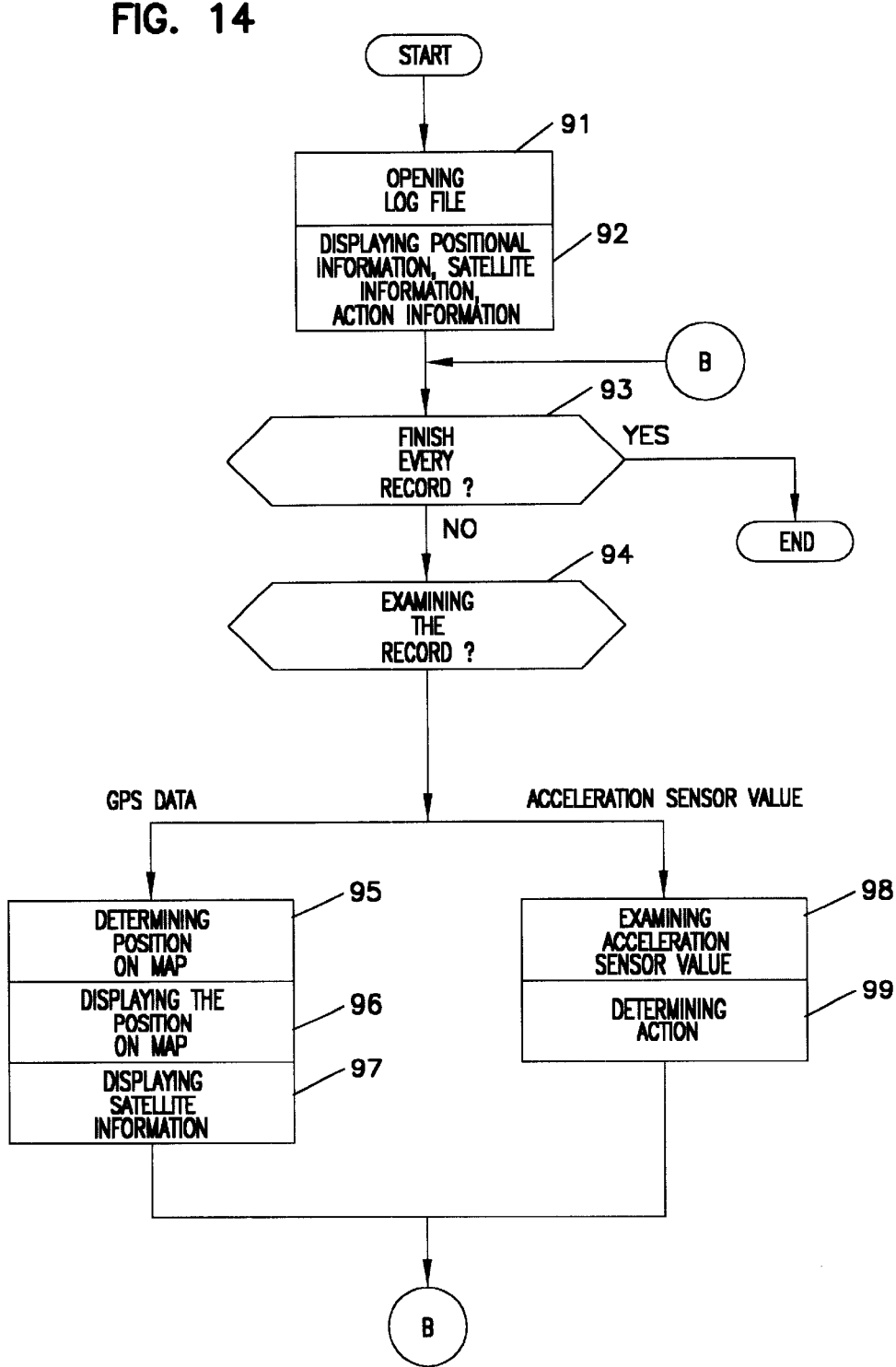
FIG. 14 is a flow chart illustrating acts involved in a preferred process of displaying historical data according to the current invention.

Now referring to FIG. 14, a flow chart illustrates acts involved in a preferred process of displaying historical data according to the current invention. The following acts are described in relation to the preferred embodiment as illustrated in FIGS. 1, 4 and 9. When a historical data display request for a particular log file 45 is made via an input unit 47, the monitoring software 50 opens the specified log file 45 in act 91. Based upon the information in the log file 45, the host unit 4 displays the positional historical information in a map window 101, the historical action information in an action window 102 and the satellite information in a satellite info window 103 in act 92. It is determined in act 93 whether or not every record in the specified log file 45 is processed. If every record is processed, the preferred process terminates.

Still referring to FIG. 14, on the other hand, if any record is remaining, it is determined in act 94 what type of the record it is. Based upon the type of the record, a different set of acts is performed. If the record is GPS data and a received portion of the GPS data includes positional information, the positional information is then written to a next available block in the memory area whose beginning address is pointed by the spot data pointer in the user info table 31 in act 95. Based upon the positional information of the GPS data, display coordinates for the sampled spot are determined also in act 95. The sampled spot is displayed in the map window 101 according to the display coordinates in act 96. Lastly, in this branch of processing, if the GPS data includes the satellite information, the satellite information is written to a next available block in the memory area whose beginning address is pointed by the satellite information pointer in the user info table 31. Based upon the satellite information, the satellite coordinates are determined for displaying in the window 103 along with the satellite number and satellite electromagnetic strength in act 97. In case the received information is acceleration value data, the acceleration value is then copied to an array of the acceleration values in act 98. Based upon the array of the acceleration values, an action of the corresponding subject is determined, and the action is stored in the action info entry of the user info table 31 in act 99. In the act 99, the action is further displayed by an icon in the display window 102. The certain action is associated with a sound generation act. In the alternative process, the above-described acts 98 and 99 are performed by a mobile communication unit 3, and the host unit 4 only displays the processed information. After the above acts, the preferred process returns to the act 93 and waits for a predetermined amount of time before reading another record.

It is to be understood, however, that even though numerous characteristics and advantages of the present invention have been set forth in the Foregoing description, together with details of the structure and function of the invention, the disclosure is illustrative only, and that although changes may be made in detail, especially in matters of shape, size and arrangement of parts, as well as implementation in software, hardware, or a combination of both, the changes are within the principles of the invention to the full extent indicated by the broad general meaning of the terms in which the appended claims are expressed.

What is claimed is:

1. A method of notifying a host unit from a mobile communication unit, the mobile communication unit monitoring a subject with the mobile communication unit, comprising the acts of:
    placing the mobile communication unit in a predetermined inactive monitoring state;
    detecting at least one of a set of predetermined conditions with respect to the subject and the mobile communication unit and generating a condition detection signal;
    placing the mobile communication unit in a predetermined active state in response to the condition detection signal;
    initiating a communication line with a predetermined global positioning system (GPS);
    requesting the predetermined GPS for a current position of the mobile communication unit in a location signal; and
    initiating a first communication line with the host unit for transmitting the condition detection signal and the location signal.

2. The method of notifying a host unit according to claim 1 wherein the set of the predetermined conditions includes that the mobile communication unit is removed from the subject.

3. The method of notifying a host unit according to claim 1 wherein the set of the predetermined conditions includes that the mobile communication unit is not properly functioning.

4. The method of notifying a host unit according to claim 1 wherein the set of the predetermined conditions includes that the subject has a certain vital sign outside a predetermined numerical range.

5. The method of notifying a host unit according to claim 4 wherein the vital sign includes a heart beat, a blood pressure level, and mobility pattern.

6. The method of notifying a host unit according to claim 1 wherein the set of the predetermined conditions includes that the subject is exposed to certain environmental harm.

7. The method of notifying a host unit according to claim 1 wherein the environmental harm includes that excess water and temperature outside a predetermined temperature range.

8. The method of notifying a host unit according to claim 1 wherein the set of the predetermined conditions includes that the subject experiences a sudden impact.

9. The method of notifying a host unit according to claim 1 wherein the set of the predetermined conditions includes that the subject experiences a certain amount of acceleration.

10. The method of notifying a host unit according to claim 1 wherein the host unit initiates the detecting act on demand.

11. The method of notifying a host unit according to claim 1 wherein the detecting act is continuous.

12. The method of notifying a host unit according to claim 1 wherein the host communicates with a plurality of uniquely identified mobile communication units.

13. The method of notifying a host unit according to claim 1 further comprising an additional act of displaying the location signal and the condition detection signal.

14. The method of notifying a host unit according to claim 1 further comprising an additional act of generating a predetermined sound based upon the location signal and the condition detection signal.

15. The method of notifying a host unit according to claim 1 wherein the predetermined inactive monitoring state conserves resources of the mobile communication unit.

16. The method of notifying a host unit according to claim 15 wherein the host sends a series of host commands to the mobile communication unit at a time, each of the commands specifying a corresponding predetermined task to be performed by the mobile communication unit.

17. The method of notifying a host unit according to claim 16 wherein the mobile communication unit stores the host commands.

18. The method of notifying a host unit according to claim 1 wherein the predetermined inactive monitoring state conserves resources of the host unit.

19. The method of notifying a host unit according to claim 18 wherein the mobile communication unit sends a series of terminal commands to the host unit at a time, each of the commands specifying a corresponding predetermined task to be performed by the host unit.

20. The method of notifying a host unit according to claim 19 wherein the host unit stores the terminal commands.

21. A system for notifying certain conditions associated with a subject, comprising:
    a mobile communication unit for detecting at least one of a set of predetermined conditions in relation to the subject who wears the mobile communication unit, the mobile communication being initially in a predetermined inactive monitoring state, upon detecting one of the predetermined conditions, the mobile communication unit generating a condition detection signal and changing its mode to a predetermined active state, the mobile communication unit further comprising a control unit for initiating a communication line with a predetermined global positioning system (GPS), upon establishing the communication line, the control unit requesting the predetermined GPS for a current position of the mobile communication unit in a location signal; and
    a host unit selectively in communication with the mobile communication unit for transmitting information between the mobile communication unit and the host unit, the control unit initiating a first communication line with the host unit for transmitting the condition detection signal and the location signal.

22. The system for notifying a host unit according to claim 21 wherein the mobile communication unit detects whether or not the mobile communication unit is removed from the subject.

23. The system for notifying a host unit according to claim 21 wherein the mobile communication unit detects whether or not the mobile communication unit is properly functioning.

24. The system for notifying a host unit according to claim 21 wherein the mobile communication unit detects whether or not the subject has a certain vital sign outside a predetermined numerical range.

25. The system for notifying a host unit according to claim 24 wherein the vital sign includes a heart beat, a blood pressure level, and mobility pattern.

26. The system for notifying a host unit according to claim 21 wherein the mobile communication unit detects whether or not the subject is exposed to certain environmental harm.

27. The system for notifying a host unit according to claim 26 wherein the environmental harm includes that excess water and temperature outside a predetermined temperature range.

28. The system for notifying a host unit according to claim 21 wherein the mobile communication unit detects whether or not the subject experiences a sudden impact.

29. The system for notifying a host unit according to claim 21 wherein the mobile communication unit detects whether or not the subject experiences a certain amount of acceleration.

30. The system for notifying a host unit according to claim 21 wherein the host unit initiates the mobile communication unit to detect predetermined conditions on demand.

31. The system for notifying a host unit according to claim 21 wherein the host communicates with a plurality of uniquely identified ones of the mobile communication unit.

32. The system for notifying a host unit according to claim 21 further comprising a display unit connected to the host unit for displaying the location signal and the condition detection signal.

33. The system for notifying a host unit according to claim 21 further comprising an audio unit connected to the host unit for generating a predetermined sound based upon the location signal and the condition detection signal.

34. The system for notifying a host unit according to claim 21 wherein the host sends a series of host commands to the mobile communication unit at a time, each of the commands specifying a corresponding predetermined task to be performed by the mobile communication unit.

35. The system for notifying a host unit according to claim 34 wherein the mobile communication unit stores the host commands.

36. The system for notifying a host unit according to claim 21 wherein the mobile communication unit sends a series of terminal commands to the host unit at a time, each of the commands specifying a corresponding predetermined task to be performed by the host unit.

37. The system for notifying a host unit according to claim 36 wherein the host unit stores the terminal commands.

* * * * *